(12) United States Patent
Coville et al.

(10) Patent No.: US 7,453,555 B2
(45) Date of Patent: Nov. 18, 2008

(54) AGGREGOMETER WITH NEAR ULTRAVIOLET LIGHT SOURCE

(75) Inventors: William E. Coville, Levittown, PA (US); Donald G. Ware, Lansdale, PA (US)

(73) Assignee: Bio/Data Corporation, Horsham, PA (US)

( * ) Notice: Subject to any disclaimer, the term of this patent is extended or adjusted under 35 U.S.C. 154(b) by 13 days.

(21) Appl. No.: 11/438,722

(22) Filed: May 22, 2006

(65) Prior Publication Data

US 2006/0279725 A1 Dec. 14, 2006

Related U.S. Application Data

(60) Provisional application No. 60/683,284, filed on May 20, 2005.

(51) Int. Cl.
*G01N 33/48* (2006.01)
(52) U.S. Cl. .......................................... 356/39; 356/40
(58) Field of Classification Search ........................ None
See application file for complete search history.

(56) References Cited

U.S. PATENT DOCUMENTS

| | | | |
|---|---|---|---|
| 4,305,659 A | | 12/1981 | Bilstad et al. |
| 4,936,674 A | | 6/1990 | Ikeda et al. |
| 5,072,610 A | * | 12/1991 | Martinoli et al. ........... 73/53.01 |
| 5,156,974 A | | 10/1992 | Grossman et al. |
| 5,422,720 A | * | 6/1995 | Berndt ....................... 356/343 |
| 5,590,052 A | * | 12/1996 | Kopf-Sill et al. ............ 700/266 |
| 6,043,871 A | | 3/2000 | Solen et al. |
| 6,064,474 A | * | 5/2000 | Lee et al. ....................... 356/39 |
| 6,101,406 A | * | 8/2000 | Hacker et al. ................ 600/322 |
| 6,254,784 B1 | * | 7/2001 | Nayak et al. ................. 210/745 |
| 6,723,554 B1 | | 4/2004 | Gaillon et al. |
| 6,770,883 B2 | * | 8/2004 | Mc Neal et al. ........... 250/341.1 |
| 2002/0014462 A1 | * | 2/2002 | Muller ....................... 210/745 |
| 2002/0028517 A1 | | 3/2002 | Brady et al. |
| 2004/0219680 A1 | | 11/2004 | Carroll et al. |
| 2005/0094127 A1 | * | 5/2005 | O'mahony et al. ............. 356/39 |

* cited by examiner

*Primary Examiner*—Michael P Stafira
(74) *Attorney, Agent, or Firm*—Volpe and Koenig PC

(57) ABSTRACT

An aggregometer has a radiation path along which radiation can pass, a sample receiving area located along the radiation path, a short-wavelength LED that transmits radiation along the radiation path through the sample receiving area, a detector positioned along the radiation path for detecting radiation transmitted from the short-wavelength LED, and a processor that controls intensity of radiation transmitted from the short-wavelength LED.

12 Claims, 5 Drawing Sheets

(PRIOR ART)

AGGREGOMETER WITH NEAR ULTRAVIOLET LIGHT SOURCE

CROSS REFERENCE TO RELATED APPLICATION(S)

This application claims the benefit of U.S. Provisional Application No. 60/683,284 filed May 20, 2005, which is incorporated by reference as if fully set forth.

BACKGROUND

Aggregation is a technique that uses turbidimetry to measure transmission of light through a homogenous suspension of particles. Aggregometers are typically used in platelet aggregation testing. For example, by measuring changes in light associated with the aggregation of platelets in plasma, these devices are useful in evaluating bleeding disorders by measuring how quickly and to what extent platelets in a sample aggregate (clump), a procedure originally developed in 1962 by Born.

Aggregometers usually utilize light sources producing wavelengths at or about 600 nm. In the past, these light sources were white light lamps with filters, but more recently red light emitting diodes (LEDs) having wavelengths between 600-626 nm are typical. The instrumentation for turbidometric measurements, particularly for platelet aggregometry, has not changed much since the 1980s.

The technique of platelet aggregation is now being used for many more applications such as: developing, dosing and monitoring anti-platelet drugs; testing other drugs and therapies for their impact on platelet aggregation, cellular-cellular and vascular-cellular interactions; understanding molecular mechanisms; and testing materials for thrombogenicity and biocompatibility. Platelet aggregation is also being used to obtain more precise results in various assays including the von Willebrand Assay, which was originally developed as a screening assay.

Coagulation is the study of the rate of fibrin formation. Specific reagents are added to plasma to measure effects on the coagulation factors (proteins) to initiate the conversion of Factor I, fibrinogen (protein) to fibrin. The result is commonly referred to as a clot. Fibrin is a stranded, solid material that, when in-vivo works in concert with platelets to form the plug that maintains vascular integrity and seals vascular injuries (bleeding). Fibrin strands being small solid materials have been found to be better detected by a shorter wavelength light source such as the short-wavelength LED described above. In coagulation, the amount of fibrin produced is relative to the physiological condition of the patient.

The devices known in the art for performing platelet aggregation, coagulation studies, and similar testing are currently being used beyond their inherent capabilities. It would be desirable to provide a more sensitive, less operator and technique dependent analyzer for platelet aggregation testing.

SUMMARY

To address these needs, the applicant has invented an aggregometer comprising: a radiation path along which radiation can pass, a sample receiving area located along the radiation path, a short-wavelength LED that transmits radiation along the radiation path through the sample receiving area, a detector positioned along the radiation path for detecting radiation transmitted from the short-wavelength LED, and a processor that controls intensity of radiation transmitted from the short-wavelength LED.

BRIEF DESCRIPTION OF THE DRAWING(S)

DETAILED DESCRIPTION OF THE PREFERRED EMBODIMENTS

Figure 1:
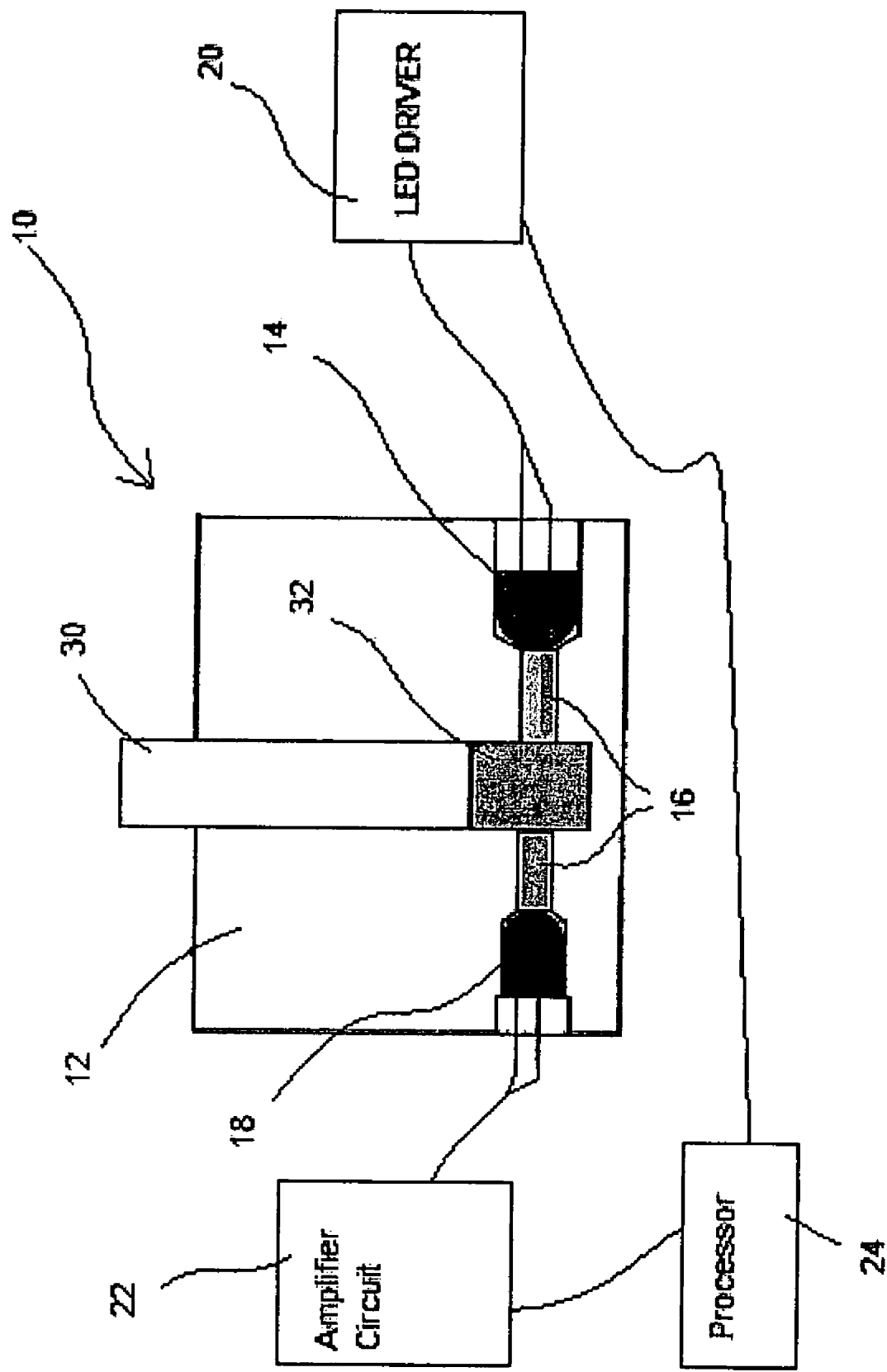
FIG. 1 is a diagrammatic view of an aggregometer according to a preferred embodiment of the present invention.

Certain terminology is used in the following description for convenience only and is not considered limiting. Words such as "front", "back", "top" and "bottom" designate directions in the drawings to which reference is made. This terminology includes the words specifically noted above, derivatives thereof and words of similar import. Additionally, the terms "a" and "one" are defined as including one or more of the referenced item unless specifically noted.

The preferred embodiments of the present invention are described below with reference to the drawing figures where like numerals represent like elements throughout and in the attached Appendix.

Referring to FIG. 1 a diagrammatic view of an aggregometer 10 according to a preferred embodiment of the present invention is shown. The aggregometer 10 includes an incubation sample receiving area or block 12 for receiving a container such as a test tube 30 containing a sample 32.

A short wavelength light emitting diode (LED) 14 is preferably positioned within the incubation block 12 to direct radiation (light) along a radiation path 16 through the sample 32. The short wavelength LED is preferably of the type producing radiation wavelengths in a range between approximately 275 and 500 nm. This range crosses from the UV to the visible spectrum. More preferably, the LED is of the type which produces wavelengths in the range between approximately 350 and 450 nm, and most preferably an LED producing wavelengths between 390 and 410 nm (near ultraviolet) is utilized.

A detector 18 is positioned to receive radiation emitted from the LED 14 through the sample 32 along the light path 16. The detector is preferably located in or in proximity to the incubation block 12.

An LED driver 20 is connected to the LED 14 to provide a signal to operate the LED 14. The driver 20 is preferably configured to provide nominal intensity (transmission level) of the LED 14. An amplifier circuit 22 is connected to the detector 18 for forwarding information regarding the detected radiation to a processor 24 for evaluation. The detector amplifier circuitry 22 is preferably configured to adjust the transmission level to a nominal level.

Figure 2:
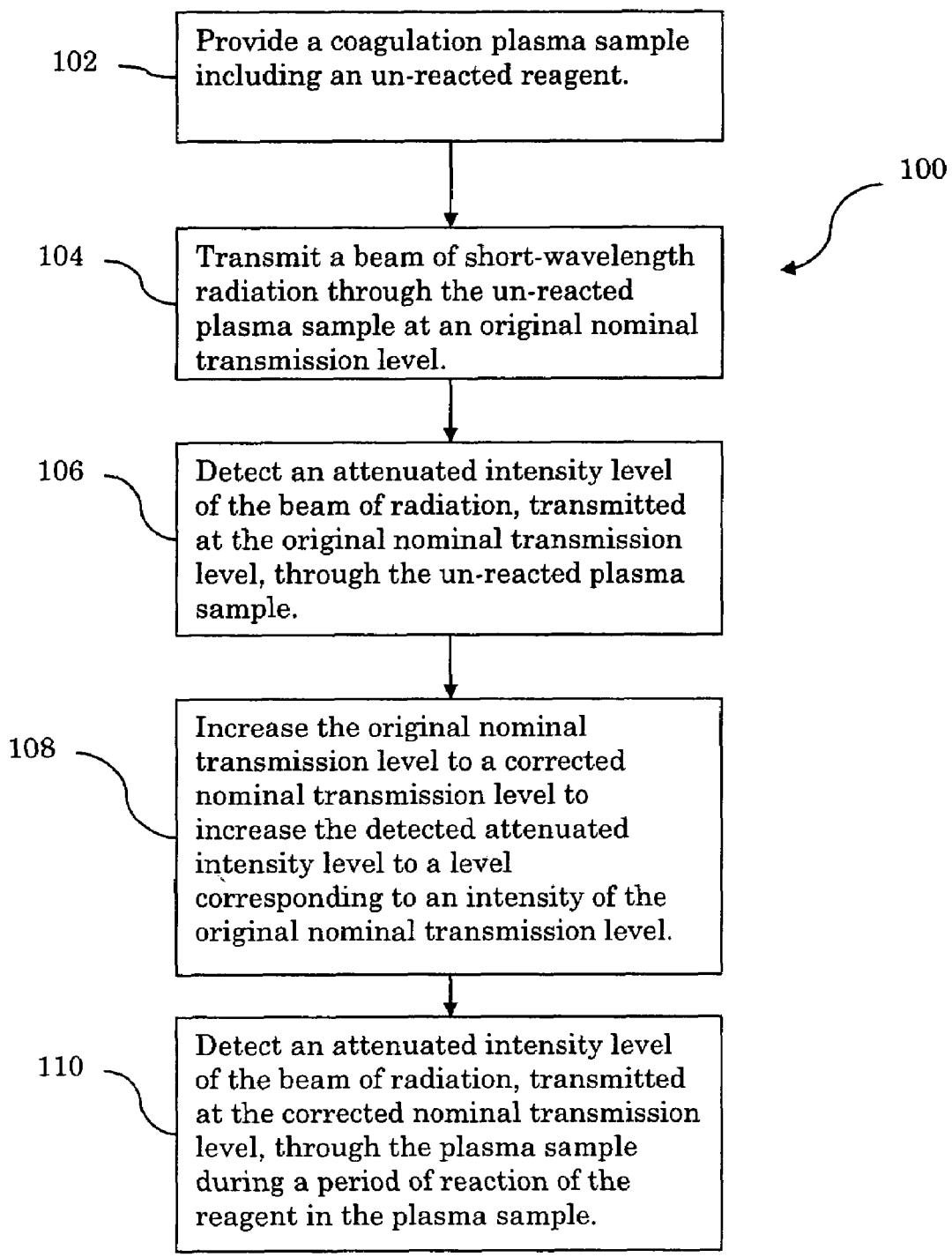
FIG. 2 is a diagram depicting a method of determining attenuation of a beam of radiation attributable to products of a plasma sample according to a preferred embodiment of the present invention.

Referring to FIG. 2, a flowchart depicting a method 100 for testing a fluid according to a preferred embodiment of the present invention is shown. The method includes providing a coagulation plasma sample including an un-reacted reagent (step 102). A beam of short-wavelength radiation is emitted from a source through the plasma sample at an original nominal transmission level (step 104). Preferably, radiation having wavelengths between 275 and 500 nm is transmitted through the sample. More preferably, radiation between 350 and 450 nm is transmitted, and most preferably radiation between 390 and 410 nm is transmitted. Preferably a narrow beam of light is transmitted, such as the light emitted by an LED. An attenuated intensity level of the beam of radiation, transmitted at the original nominal transmission level, is detected through the un-reacted plasma sample (step 106). The original nominal transmission level is increased to a corrected nominal transmission level to increase the detected attenuated intensity level to a level corresponding to an intensity of the original nominal transmission level (step 108). In this manner, at the corrected nominal transmission level, the detected radiation which passed through the un-reacted plasma sample is approximately equal to the radiation emitted at the original nominal transmission level. Accordingly, the attenuation occurring in the un-reacted sample is compensated for (corrected) by increasing the transmission level. In a step 110, an attenuated intensity level of the beam of radiation, transmitted at the corrected nominal transmission level, is detected through the plasma sample during a period of reaction of the reagent in the plasma to determine the attenuation attributable to products of the reacting reagent. The corrected nominal transmission level is preferably set at least high enough such that radiation is detectable through the sample during the entire reaction period.

Figure 3:
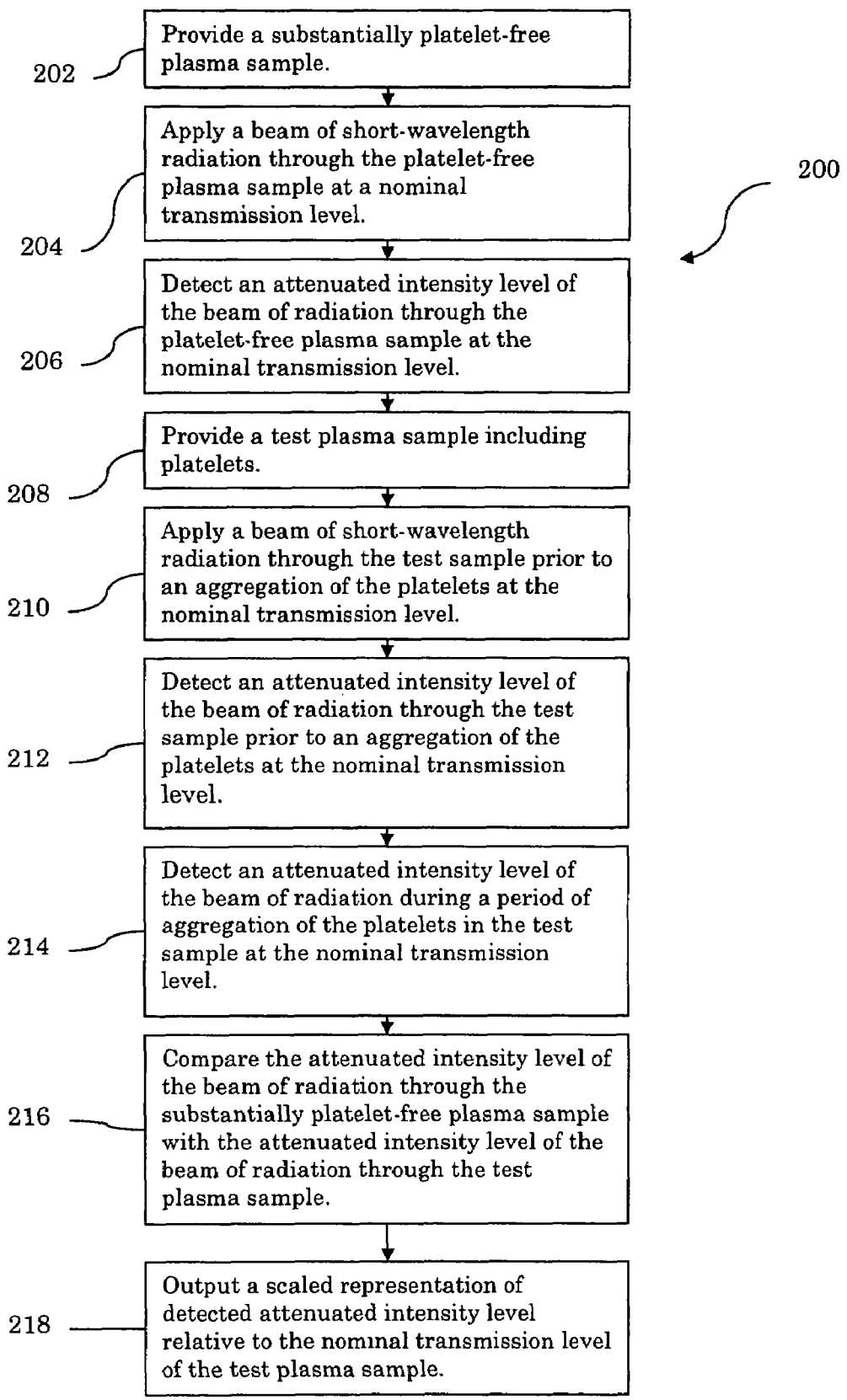
FIG. 3 is a diagram depicting a method of determining attenuation of a beam of radiation attributable to products of a plasma sample according to another preferred embodiment of the present invention.

Referring to FIG. 3, a flowchart depicting a method 200 for testing a fluid according to another preferred embodiment of the present invention is shown. The method includes providing a substantially platelet-free plasma sample (step 202). A beam of short-wavelength radiation is applied through the platelet-free plasma sample at a predetermined transmission level (step 204). Preferably, radiation having wavelengths between 275 and 500 nm is transmitted through the sample. More preferably, radiation between 350 and 450 nm is transmitted, and most preferably radiation between 390 and 410 nm is transmitted. Preferably a narrow beam of light is transmitted, such as the light emitted by an LED. The beam of radiation passing through the platelet-free plasma sample at the nominal transmission level is detected (step 206). A new test plasma sample including platelets is provided (step 208), or alternatively, platelets are added to the platelet-free plasma sample. A beam of short-wavelength radiation is applied through the test plasma sample at the nominal transmission level prior to aggregation of the platelets (step 210), and an attenuated intensity level of the beam of radiation through the test sample is detected (step 212). An attenuated intensity level of the beam of radiation at the nominal transmission level during a period of aggregation of the platelets in the test sample is detected (step 214). The attenuated intensity level of the beam of radiation through the substantially platelet-free plasma sample is compared with the attenuated intensity level of the beam of radiation through the test plasma sample (containing platelets) to determine the attenuated intensity level attributable to aggregated and non-aggregated platelets (step 216). In a step 218, a scaled representation of the detected attenuated intensity level relative to the nominal transmission level is outputted. For example, a computer processor can output a representation of the detected attenuated intensity level relative to the nominal transmission level multiplied by a factor to correct for differences in sample quality. The nominal transmission level is preferably set at least high enough such that radiation is detectable through the sample during the entire reaction period.

EXAMPLES AND TESTING

In testing, aggregometers using a shorter wavelength (395 nm) LED were found to function in a superior manner for platelet aggregation and coagulation tests.

The shorter wavelength LED allows for a higher level of sensitivity during testing. Accordingly, less amplification of the optical transmission signal compared to either white light or lamps with filters or red LEDs (626-660 nM) is required, thus allowing for a greater range of adjustment of the optical system. This brings improvements to an optical analyzer using a short-wavelength LED. First, the hardware, circuitry, and software are simplified. When a basic signal requires little amplification, fewer components or software routines are required. Second, there is a reduction in noise producing a cleaner signal and less errors. When a signal is amplified, the noise in the signal is also amplified and filtering (smoothing) must be performed to reduce errors caused by the noise. Smoothing increases certain types of error and decreases sensitivity. Third, the required additional hardware and software components add costly complexity to the circuits, processes, and operation.

Factor assay test methods benefit from the higher sensitivity of aggregometers utilizing short-wavelength LEDs. In these methods, reference curves are developed with a standard plasma (90-120% activity of the factor) that is serially diluted (down) to an activity of 1.56% (1:64 dilution). Tests are based on the rate of change in optical density.

Figure 4A:
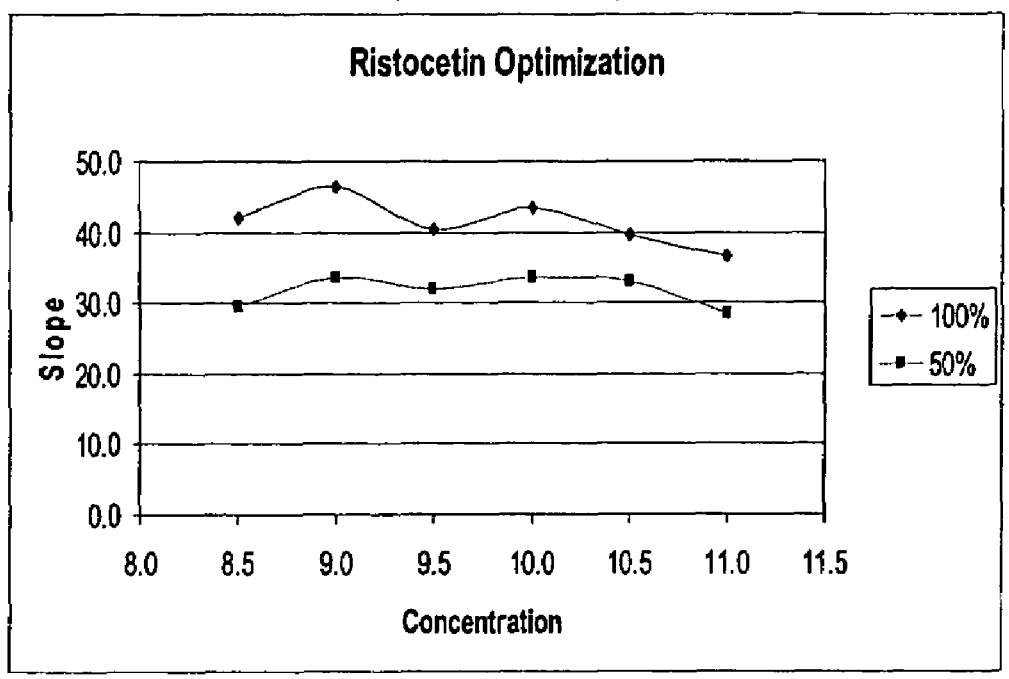
FIGS. 4a-4b are graphic plots of test results for a ristocetin dilution test using a prior art aggregometer with a 626 nm LED.
Figure 4B:
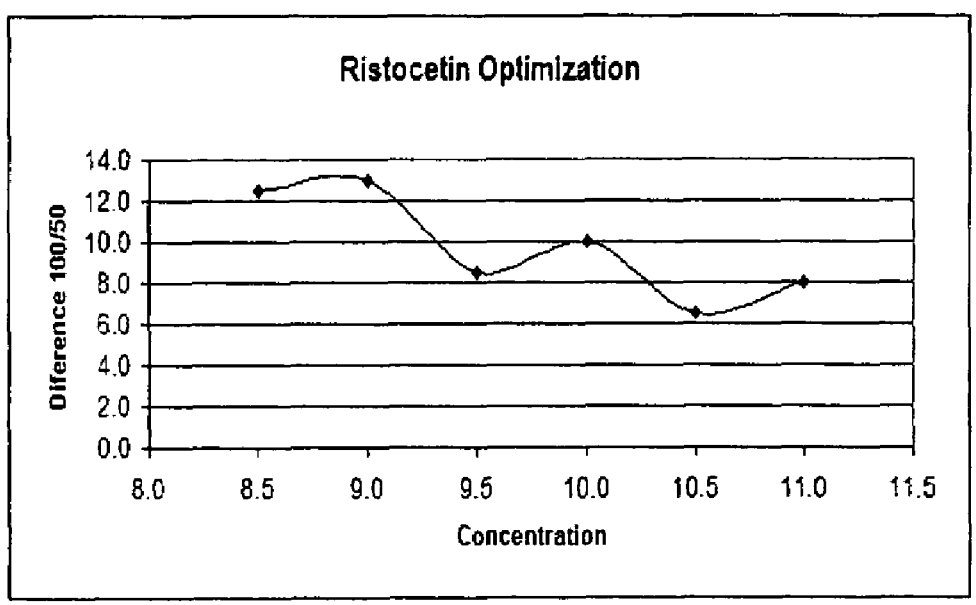

Table 1 below and FIGS. 4a and 4b provide test results of a factor assay test: a ristocetin dilution test using an aggregometer with a 626 nm (long-wavelength) LED.

TABLE 1

(PRIOR ART)
PAP-4 626 nm LED

| Ristocetin Concentration mg/ml | 100% Slope | | 100% Avg. | 50% Slope | | Avg. | Difference 100 − 50 |
|---|---|---|---|---|---|---|---|
| 8.5 | 42.0 | 42.0 | 42.0 | 29.0 | 30.0 | 29.5 | 12.5 |
| 9.0 | 47.0 | 46.0 | 46.5 | 32.0 | 35.0 | 33.5 | 13.0 |
| 9.5 | 41.0 | 40.0 | 40.5 | 33.0 | 31.0 | 32.0 | 8.5 |
| 10.0 | 41.0 | 46.0 | 43.5 | 33.0 | 34.0 | 33.5 | 10.0 |
| 10.5 | 39.0 | 40.0 | 39.5 | 31.0 | 35.0 | 33.0 | 6.5 |
| 11.0 | 41.0 | 32.0 | 36.5 | 28.0 | 29.0 | 28.5 | 8.0 |

This is a quality control test in which ristocetin/plasma are tested to select the best dilution for a lot of ristocetin reagent. The attenuation of samples was measured at 8.5 mg/ml to 11.0 mg/ml concentrations to determine a slope of each sample (see Table 1, 100% slope, 100% Avg.). The slope is known by those skilled in the art as an indicator of the rate of reaction of the ristocetin reagent. Each of the 8.5 mg/ml to 11.0 mg/ml concentration ristocetin/plasma concentrations were also respectively tested diluted to 50% (see Table 1, 50% slope, 50% Avg.). The results of Table 1 are plotted in FIGS. 4a and 4b. FIG. 4a plots the slopes for each concentration at both 100% and 50% levels. FIG. 4b plots the difference in slopes between the 100% and 50% dilution levels for each concentration. As can be seen in FIG. 4b, the difference in slope between the 100% and 50% dilution levels follows a highly irregular path using the 626 nm LED over the range of concentrations tested. Such irregularity makes reliable testing and analysis decision making difficult.

Figure 5A:
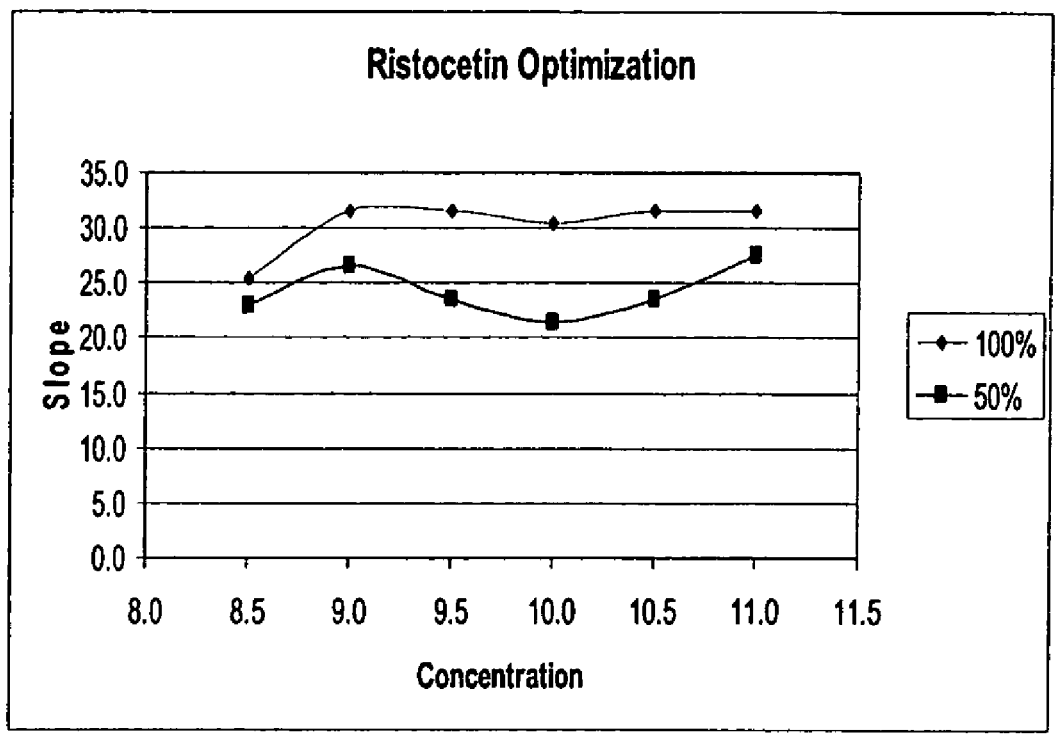
FIGS. 5a-5b are graphic plots of test results for a ristocetin dilution test using an aggregometer with a 395 nm LED.
Figure 5B:
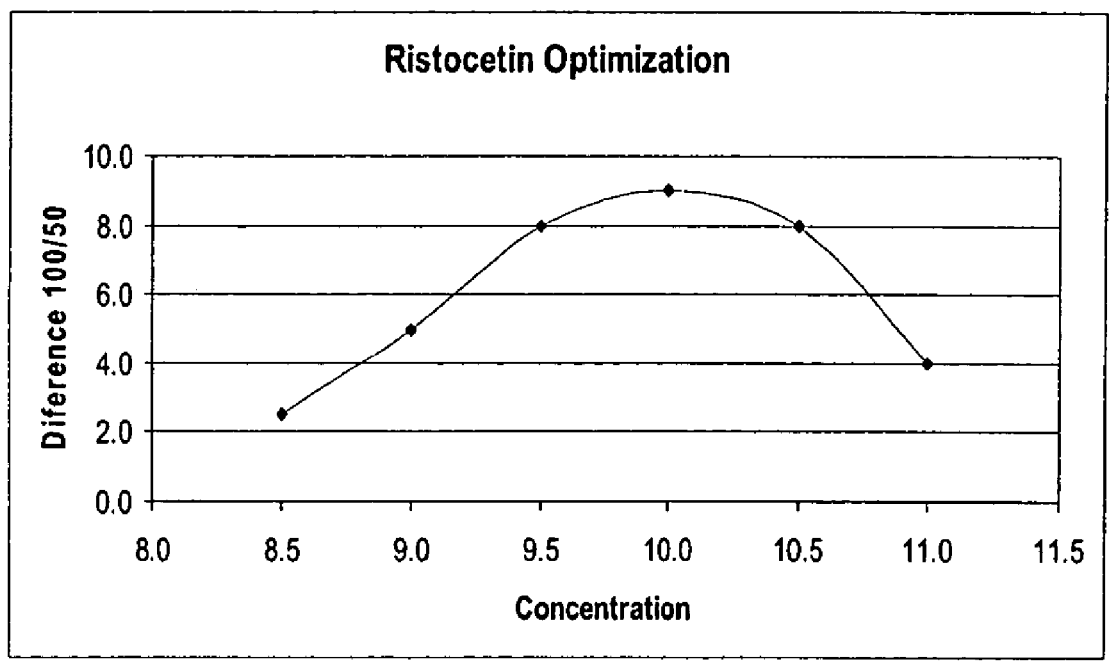

Table 2 below and FIGS. 5a and 5b show test results for a ristocetin dilution test using an aggregometer with a short-wavelength, 395 nm LED. As can be seen in FIG. 5b, the difference in slope between the 100% and 50% dilution levels follows a clear tub-shaped path allowing for reliable testing and analysis decision making. Normally, a ristocetin/plasma concentration of 10 mg/ml is preferred for a lot of ristocetin reagent because of the appreciable contrast between the 100% and 50% slopes as shown below. However, this contrast is not apparent when testing is performed using an aggregometer a 626 nm LED as shown in FIG. 4b. Accordingly the increased precision in using a short-wavelength LED is apparent. Other factor assay tests would also benefit from the use of an aggregometer having a short-wavelength LED.

TABLE 2

PAP-8E 340 nm LED

| Ristocetin Concentration mg/ml | 100% Slope | | 100% Avg. | 50% Slope | | Avg. | Difference 100 − 50 |
|---|---|---|---|---|---|---|---|
| 8.5  | 23.0 | 28.0 | 25.5 | 22.0 | 24.0 | 23.0 | 2.5 |
| 9.0  | 32.0 | 31.0 | 31.5 | 28.0 | 25.0 | 26.5 | 5.0 |
| 9.5  | 31.0 | 32.0 | 31.5 | 24.0 | 23.0 | 23.5 | 8.0 |
| 10.0 | 31.0 | 30.0 | 30.5 | 22.0 | 21.0 | 21.5 | 9.0 |
| 10.5 | 30.0 | 33.0 | 31.5 | 21.0 | 26.0 | 23.5 | 8.0 |
| 11.0 | 30.0 | 33.0 | 31.5 | 29.0 | 26.0 | 27.5 | 4.0 |

The most common use of aggregation in the United States is a test method called the Ristocetin Cofactor Assay. This assay uses standard lyophilized platelets and a plasma that contains a factor. This method uses a standard curve where the standard plasma is diluted to concentrations of 100% to 25%. The usefulness of this assay is below 40% and mostly around 10% so the method is changed to go as low as 12.5% Clinicians prefer that the assay be accurate below 10% because that is where the worst physiological problems occur.

This test method preferably uses a normal platelet rich plasma (PRP) that has 200,000 platelets per cubic mm, with 1 µL volume. At about 6 µm long (oval), the platelets are quite small.

The normal test volume for the PAP-8E using the UV LED's is 500 µL. Using this volume, and the 200,000 platelets per cubic mm, we can assume there are (500×200,000=) 100,000,000 platelets.

During testing the beam of radiation passes through about 25% of the PRP. The task then, is to measure how many and how fast this smaller percentage of the PRP reacts and aggregates. This is done by the measurement of the change in transmission between a platelet poor (PPP) blank and the platelet rich sample.

Applicant's prior art aggregometer labeled as PAP-4 views about twice as large a volume as applicant's aggregometer labeled as PAP-8E. From testing and knowledge of the market, applicant believes that this is better than any aggregometer on the market.

Using this method yields the following test data.

TABLE 3

| | % | | | | | | | |
|---|---|---|---|---|---|---|---|---|
| | 100 | | 50 | | 25 | | 12.5 | |
| | | | | % CV | | | | |
| | Agg | Slope | Agg | Slope | Agg | Slope | Agg | Slope |
| | Curve Data | | | | | | | |
| PAP-4   | 10.9 | 8.9  | 19.0 | 16.5 | 17.1 | 20.6 | — | — |
| PAP-8E  | 12.8 | 12.8 | 12.2 | 9.4  | 14.8 | 14.6 | — | — |
| | Test Data | | | | | | | |
| PAP-8E  | 11.8 | 9.8  | 10.9 | 11.3 | 11.5 | 10.9 | 14.3 | 13.6 |

Normal Aggregation Test Data:

The accepted accuracy for the Aggregation is 15% CV.

The applicant has demonstrated in its validation and testing data of normal aggregation test types that the PAP-E demonstrates general aggregation precision in two ways. The channel to channel variation in the PAP-8 E is now less than 11% CV for slope reproducibility and less than 8% CV for % aggregation reproducibility.

TABLE 4

PAP-8E AGGREGATION 340 nM LED CHANNEL TO CHANNEL DATA

| Test Type | | Epinephrine | Collagen | ADP | Arachidonic Acid |
|---|---|---|---|---|---|
| Average | Slope | 30.5 | 44.0 | 41.3 | 38.9 |
|  | % Agg. | 73.1 | 74.9 | 72.6 | 73.5 |
| Standard Deviation | Slope | 2.1 | 4.5 | 2.8 | 2.9 |
|  | % Agg. | 3.7 | 4.7 | 4.1 | 5.8 |
| CV | Slope | 7.0% | 10.2% | 6.8% | 7.3% |
|  | % Agg. | 5.1% | 6.2% | 5.6% | 7.9% |

While the preferred embodiments of the invention have been described in detail above and in the attached Figures, the invention is not limited to the specific embodiments described above, which should be considered as merely exemplary. Further modifications and extensions of the present invention may be developed, and all such modifications are deemed to be within the scope of the present invention as defined by the appended claims.

What is claimed is:

1. A method for testing a fluid comprising:
   providing a plasma sample including an un-reacted reagent;
   transmitting a beam of short-wavelength radiation through the plasma sample at a predetermined transmission level;
   detecting an attenuation of the beam of radiation at the predetermined transmission level through the un-reacted plasma sample;
   detecting an attenuation of the beam of radiation at the predetermined transmission level through the plasma sample during a period of reaction of the reagent in the plasma sample; and
   comparing the attenuation of the beam of radiation through the plasma sample during the reaction period with the beam of radiation during the period of non-reaction.

2. A method for testing a fluid comprising the steps of:
   providing a sample including an un-reacted reagent;
   transmitting a beam of short-wavelength radiation through the sample at an original transmission intensity;
   detecting an attenuated intensity of the beam of short-wavelength radiation after the beam of short-wavelength radiation passes through the un-reacted reagent;
   increasing the transmission intensity of the beam of short-wavelength radiation until the attenuated intensity corresponds to the original transmission intensity;
   allowing the un-reacted reagent to react; and
   detecting a subsequent attenuated intensity of the beam of short-wavelength radiation after the beam of short-wavelength radiation at the predetermined transmission level passes through the reagent during a time period while the reagent is reacting.

3. The method of claim 1, wherein the increased transmission intensity of the beam of short-wavelength radiation is set to a level such that radiation is detectable through the reagent during the time period.

4. The method of claim 2, wherein the short-wavelength radiation is transmitted in a wavelength range between 275 and 500 nm.

5. The method of claim 4, wherein the short-wavelength radiation is transmitted in a wavelength range between 350 and 450 nm.

6. The method of claim 5, wherein the short-wavelength radiation is transmitted in a wavelength range between 390 and 410 nm.

7. A method for testing a fluid comprising the steps of:
providing a substantially platelet-free plasma sample;
transmitting a beam of short-wavelength radiation through the substantially platelet-free plasma sample at an original transmission intensity;
detecting an attenuated intensity of the beam of short-wavelength radiation after the beam of short-wavelength radiation passes through the substantially platelet-free plasma sample;
providing a plasma sample with substantially unaggregated platelets;
transmitting a beam of short-wavelength radiation through the sample with substantially unaggregated platelets at the original transmission intensity;
detecting an attenuated intensity of the beam of short-wavelength radiation after the beam of short-wavelength radiation passes through the plasma sample with substantially unaggregated platelets; and
detecting an attenuated intensity of the beam of short-wavelength radiation after the beam of short-wavelength radiation passes through the plasma sample during a period of aggregation of the platelets.

8. The method of claim 7, further comprising the step of:
comparing (1) the detected attenuated intensity of the beam of short-wavelength radiation after the beam of short-wavelength radiation passes through the substantially platelet-free plasma sample with (A) the detected attenuated intensity of the beam of short-wavelength radiation after the beam of short-wavelength radiation passes through the plasma sample with substantially unaggregated platelets and/or
(B) the detected attenuated intensity of the beam of short-wavelength radiation after the beam of short-wavelength radiation passes through the plasma sample during a period of aggregation of the platelets.

9. The method of claim 8, further comprising the step of:
outputting a comparison between (1) the intensity of the beam of short-wavelength radiation passing through the substantially platelet-free plasma sample at the original transmission intensity, with (A) the detected attenuated intensity of the beam of short-wavelength radiation after the beam of short-wavelength radiation passes through the plasma sample with substantially unaggregated platelets and/or
(B) the detected attenuated intensity of the beam of short-wavelength radiation after the beam of short-wavelength radiation passes through the plasma sample during a period of aggregation of the platelets.

10. The method of claim 7, wherein the short-wavelength radiation is transmitted in a wavelength range between 275 and 500 nm.

11. The method of claim 7, wherein the short-wavelength radiation is transmitted in a wavelength range between 350 and 450 nm.

12. The method of claim 7, wherein the short-wavelength radiation is transmitted in a wavelength range between 390 and 410 nm.

* * * * *